US012766228B2

(12) United States Patent
Pack et al.

(10) Patent No.: US 12,766,228 B2
(45) Date of Patent: Oct. 20, 2026

(54) SURGICAL ARTICLE FORMED FROM FINE GRAINED TUNGSTEN CARBIDE IN NICKEL MATRIX

(71) Applicants: THINK SURGICAL, INC., Fremont, CA (US); EXTRAMET PRODUCTS LLC, Latrobe, PA (US)

(72) Inventors: Timothy Pack, Fremont, CA (US); Christopher Douglas, Latrobe, PA (US); Joel Zuhars, Fremont, CA (US); Micah Forstein, Fremont, CA (US)

(73) Assignees: Think Surgical, Inc., Fremont, CA (US); Extramet Products LLC, Latrobe, PA (US)

( * ) Notice: Subject to any disclaimer, the term of this patent is extended or adjusted under 35 U.S.C. 154(b) by 75 days.

(21) Appl. No.: 18/950,353

(22) Filed: Nov. 18, 2024

(65) Prior Publication Data

US 2025/0073377 A1 Mar. 6, 2025

Related U.S. Application Data

(63) Continuation-in-part of application No. 17/312,086, filed as application No. PCT/US2019/065578 on Dec. 11, 2019, now Pat. No. 12,171,913.
(Continued)

(51) Int. Cl.

| | |
|---|---|
| ***A61L 31/02*** | (2006.01) |
| ***A61B 17/00*** | (2006.01) |

(Continued)

(52) U.S. Cl.
CPC ........... *A61L 31/026* (2013.01); *A61L 31/022* (2013.01); *A61B 2017/00526* (2013.01);
(Continued)

(58) Field of Classification Search
CPC ....... C22C 29/067; C22C 29/08; C22C 1/055; C22C 28/08; A61L 27/047; A61L 27/10;
(Continued)

(56) References Cited

U.S. PATENT DOCUMENTS

| | | | |
|---|---|---|---|
| 6,521,353 B1 * | 2/2003 | Majagi | C22C 29/08 428/565 |
| 8,801,816 B2 | 8/2014 | Okuno et al. | |

(Continued)

FOREIGN PATENT DOCUMENTS

| | | |
|---|---|---|
| CN | 1003173673 A | 6/2013 |
| CN | 106077610 A | 11/2016 |

(Continued)

OTHER PUBLICATIONS

Office Action issued in corresponding Japanese Patent Appln. No. 2021-531252, dated Sep. 6, 2023.
(Continued)

*Primary Examiner* — Marcela I. Shirsat
(74) *Attorney, Agent, or Firm* — MaxGoLaw PLLC

(57) ABSTRACT

A biocompatible surgical article is provided for cutting biological tissue or implantation in contact therewith. The surgical article has a composition of tungsten carbide—nickel with a percentage of additional metal carbides present. A typical composition in total weight percentages is WC 85 to 95%, $Cr_3C_2$, $Mo_2C$, VC each alone or in combination being present from 0 to 2%, and Ni constituting the remainder. The composition is formed to have an mean grain size of between 200 and 800 nm with a particle dispersion index (PdI) corresponding to (the square of the standard deviation)/(mean grain size) of between 0 and 0.6, and in some embodiments between 0.02 and 0.2.

14 Claims, 8 Drawing Sheets

Related U.S. Application Data

(60) Provisional application No. 62/779,186, filed on Dec. 13, 2018.

(51) Int. Cl.

| | |
|---|---|
| ***A61B 17/16*** | (2006.01) |
| ***A61B 17/32*** | (2006.01) |
| ***A61B 17/34*** | (2006.01) |
| ***A61L 27/04*** | (2006.01) |
| ***A61L 27/42*** | (2006.01) |
| ***A61L 31/12*** | (2006.01) |
| ***A61L 31/14*** | (2006.01) |
| ***C22C 1/055*** | (2023.01) |
| ***C22C 29/06*** | (2006.01) |
| ***C22C 29/08*** | (2006.01) |

(52) U.S. Cl.

CPC ............... *A61B 2017/00836* (2013.01); *A61B 2017/1602* (2013.01); *A61B 17/1615* (2013.01); *A61B 17/32002* (2013.01); *A61B 17/320068* (2013.01); *A61B 17/34* (2013.01); *A61L 27/047* (2013.01); *A61L 27/427* (2013.01); *A61L 31/124* (2013.01); *A61L 31/14* (2013.01); *A61L 2430/24* (2013.01); *B22F 2998/10* (2013.01); *C22C 1/055* (2013.01); *C22C 29/067* (2013.01); *C22C 29/08* (2013.01)

(58) Field of Classification Search

CPC .... A61L 27/427; A61L 31/022; A61L 31/026; A61L 31/124; A61L 31/14; A61B 17/1615; A61B 17/320068; A61B 17/14; A61B 17/32002; A61B 17/34; A61B 17/58; A61B 17/8866; A61B 2017/00526; A61B 2017/00836; A61B 2017/00889; A61B 2017/1602; A61B 2017/320082; A61F 2/30; A61F 2002/30003; B22F 2005/001; B22F 2998/10; B22F 2999/00

USPC .................................................... 75/240, 242

See application file for complete search history.

(56) References Cited

U.S. PATENT DOCUMENTS

| | | | | |
|---|---|---|---|---|
| 11,292,723 | B2 | 4/2022 | Sauberlich et al. | |
| 12,171,913 | B2 * | 12/2024 | Pack | A61L 27/047 |
| 2002/0136894 | A1 | 9/2002 | Itsukaichi | C23C 4/06 264/6 |
| 2006/0155314 | A1 | 7/2006 | Pappas et al. | |
| 2006/0184251 | A1 | 8/2006 | Zhang et al. | |
| 2007/0082229 | A1 * | 4/2007 | Mirchandani | A44C 27/002 419/13 |
| 2013/0287625 | A1 | 10/2013 | Wada et al. | |
| 2014/0225330 | A1 * | 8/2014 | Saito | F16J 9/26 277/442 |
| 2016/0030067 | A1 * | 2/2016 | Frey | A61B 50/33 606/86 A |
| 2016/0157964 | A1 * | 6/2016 | Suttin | A61C 8/0089 901/41 |
| 2016/0281202 | A1 | 9/2016 | Saito et al. | |
| 2017/0040205 | A1 | 2/2017 | Heister et al. | |

FOREIGN PATENT DOCUMENTS

| | | | |
|---|---|---|---|
| CN | 106906397 | A | 6/2017 |
| CN | 107312961 | A | 11/2017 |
| EP | 2227155 | | 7/2016 |
| GB | 2393449 | A | 3/2004 |
| JP | S6176645 | A | 4/1986 |
| JP | S6176646 | A | 4/1986 |
| JP | 2013213259 | A | 10/2013 |
| KR | 101581081 81 | | 12/2015 |
| KR | 101859644 | B1 | 5/2018 |
| KR | 1020180095909 | A | 8/2018 |
| WO | 2017108610 | A1 | 6/2017 |
| WO | 2018050474 | A1 | 3/2018 |
| WO | 2016134266 | A1 | 8/2018 |

OTHER PUBLICATIONS

Int'l Search Report for PCT/US2019/065578, dated Apr. 9, 2020.

Supplementary EP Search Report issued in EP19895891, dated Aug. 8, 2022.

Lauwers, et al., "Influence of the Composition of WC-Based Cermets on Manufacturability by Wire-EDM", Journal of Manufacturing Processes, Society of Manufacturing Engineers, Dearborn, MI, US, vol. 8, No. 2, Jan. 1, 2006 (Jan. 1, 2006) , pp. 83-89 (Abstract).

* cited by examiner

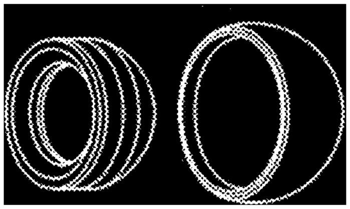
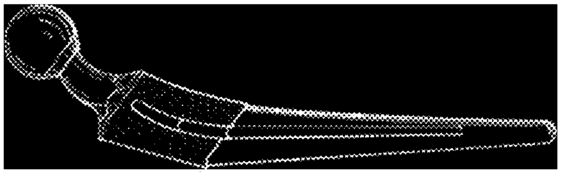
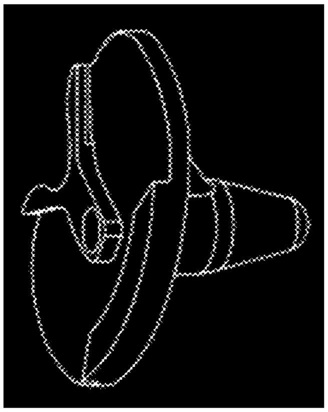
FIG. 3B
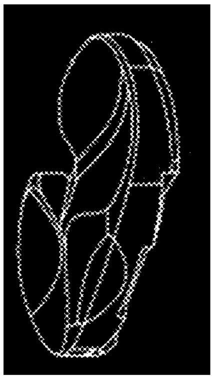
FIG. 3C
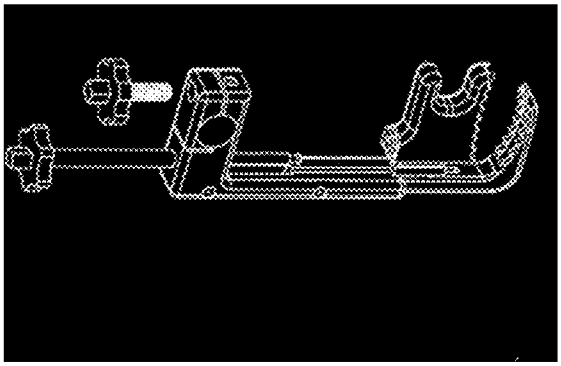
FIG. 3A
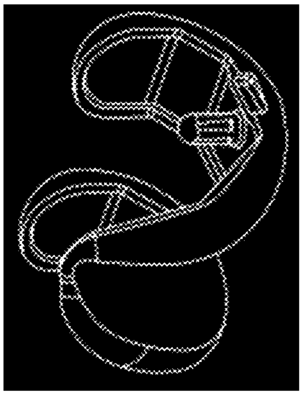

SURGICAL ARTICLE FORMED FROM FINE GRAINED TUNGSTEN CARBIDE IN NICKEL MATRIX

RELATED APPLICATIONS

This application is a continuation-in-part of U.S. patent application Ser. No. 17/312,086, filed Jun. 9, 2021, which in turn is a US National phase filing of PCT Application Serial Number PCT/US2019/065578, filed Dec. 11, 2019, which in turn claims priority benefit to U.S. Provisional Application Ser. No. 62/779,186, filed Dec. 13, 2018, the contents of which are hereby incorporated by reference.

FIELD OF THE INVENTION

This invention relates generally to a surgical article operative to cut or implant in body tissue and in particular, to a surgical article based on a fine grained tungsten carbide in a nickel matrix.

BACKGROUND OF THE INVENTION

An end effector is an essential distal portion of a robotic surgery system, as well as manual surgical tools with the common feature being an electrical driving unit to induce rotational or lateral movement of the cutting tool. In order to remove tissue, the end effector is actuated and contacts the tissue to be removed. When the end effector is contacting bone, the actuated end effector can induce frictional heating that can damage retained tissue, while differences in tissues density being cut simultaneously can induce the end effector to preferentially veer from a desired cut path.

Conventional end effectors are fabricated from stainless steel as the steel is generally economical and can be shaped to define a sharp cutting surface while tolerating the conditions and sterilization without physical degradation. Unfortunately, stainless steel end effectors suffer dulling in the course of a procedure that exacerbates the aforementioned problems. Conventional thought is that the comparative rigidity of the stainless steel is important to avoid significant deviation from the tool axis during machining.

Likewise, implant formation has traditionally relied on stainless steel or titanium to form metal structures that both have limitations. Type 316L stainless steel is routinely used owing to its corrosion resistance when in direct contact with biological fluid as intracorporeal corrosion often leads to infection. This type of stainless steel is particularly effective as a surgical implant when in cold-worked condition and lacking inclusions.

Type 316L stainless steel selected for the purpose of surgical implants contains approximately 17 to 19% of chromium and 14% nickel. With surgical implants, molybdenum is added to the stainless steel alloy to form a protective layer sheltering the metal from exposure to an acidic biological fluid environment. Corrosion resistance can also be achieved with the element carbon but only when the carbon is in a solid solution state.

Compared to stainless steel alloys that have been in medical practice since the early 1900s, titanium is relatively new in its application as a medical implant for the replacement of a biological tissue. Unfortunately, titanium is easily contaminated if exposed to hydrogen, nitrogen, or oxygen, which can influence the corrosion process in this metal and may compromise titanium's use in certain medical procedures. The 1960s experienced a shift in the selection of best-fit metals for surgical implants with titanium being a popular choice. Yet, the durability of such implants is a factor in the longevity of an implant before revisionary procedures are required.

The use of cemented carbide materials has been considered as an alternative, yet to render them biocompatible such materials have been depleted in both cobalt and nickel, as detailed in U.S. Patent Publication 2007/0082229. In still other instances, surgical instruments formed of tungsten carbide in a nickel matrix have been contemplated with the proviso that porosity be limited to prevent microbe residence therein, as detailed in U.S. Patent Publication 2006/0155314. The criticality of these characteristics to a surgical article have been disputed in field.

Thus, there exists a need for a new material from which such surgical articles are formed. There further exists a need for such articles formed of fine-grained tungsten carbide in nickel matrix that affords biocompatibility. There further exists a need for such articles that are formed as a monolithic article, as opposed to having been formed from disparate materials that are subsequently joined.

SUMMARY OF THE INVENTION

A surgical article has a composition having a desired shape and a mean grain size. The composition includes by weight: tungsten carbide (WC) present from 85 to 95 total weight percent; $Cr_3C_2$ and $Mo_2C$ each alone, or in combination being present from 0 to 2 total weight percent, and Ni constituting the remainder; the average grain size being between 200 and 1200 nm with a particle dispersion index of between 0.2 and 1.2.

A method is provided for cutting tissue of a subject in the course of a surgical procedure that includes forming a surgical article as disclosed below having a tissue contacting portion, and rotating or oscillating the surgical article while the tissue contacting portion engages the tissue of the subject.

A method is provided for modifying tissue of a subject in the course of a surgical procedure that includes forming a surgical article as disclosed below, placing the surgical article in contact with the tissue of the subject, and retaining the surgical article in vivo and in contact with the tissue of the subject.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Dimensions of components and features shown in the figures are generally chosen for convenience and clarity of presentation and are not necessarily shown to scale. The figures are listed below.

FIG. 3A is a perspective view of an inventive surgical article in the form of a bone clamp;

FIG. 3B is a perspective view of an inventive surgical article in the form of hip implants;

FIG. 3C is a perspective view of an inventive surgical article in the form of knee implants;

DETAILED DESCRIPTION OF THE INVENTION

Figure 1B:
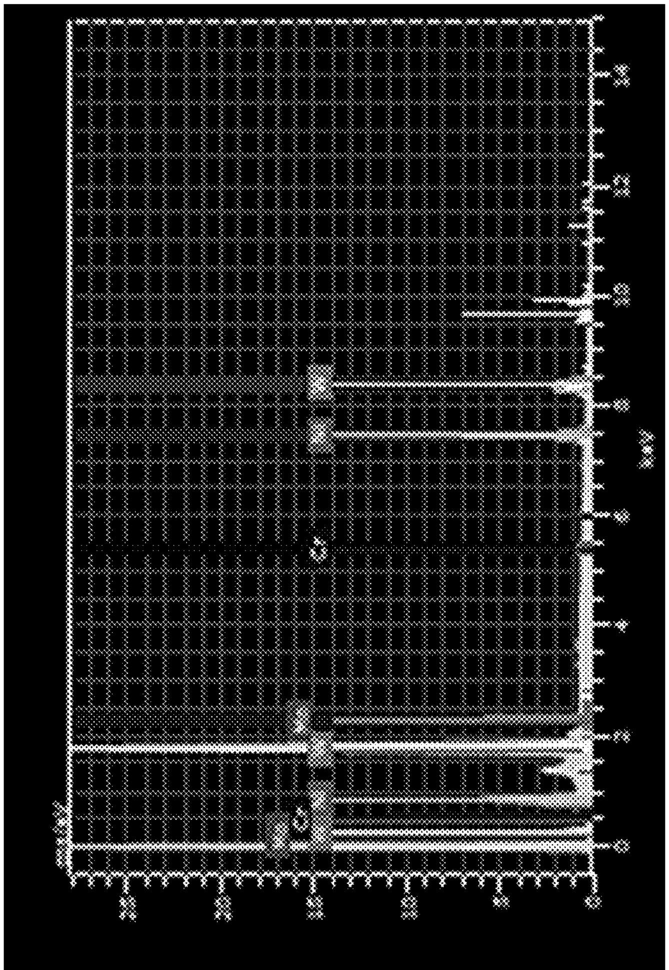
FIG. 1B is an energy dispersive spectroscopy intensity plot of the area of FIG. 1A defined by the border therein with the various peak energies labelled with the corresponding elements.

The present invention has utility as a biocompatible surgical article for cutting biological tissue or implantation in contact therewith. It has been surprisingly found that a fine grained majority tungsten carbide in nickel matrix affords a balance of biocompatibility and attractive cutting properties irrespective of porosity and a high nickel content. The resulting surgical article is readily formed from a single piece of material thereby avoiding excess machining operations and the weaknesses associated with joints.

The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment may be deleted from that embodiment. In addition, numerous variations and additions to the embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof.

It is to be understood that in instances where a range of values are provided herein, that range is intended to encompass not only the end point values of the range, but also intermediate values of the range as explicitly being included within the range and varying by the last significant figure of the range. By way of example, a recited range of from 1 to 4 is intended to include 1-2, 1-3, 2-3, 2-4, 3-4, and 1-4.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

Unless indicated otherwise, explicitly or by context, the following terms are used herein as set forth below.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

As used herein, a "surgical article" is defined as an implement, instrument, implant/prosthesis, tool, or any other device intended to contact tissue. Examples of surgical articles are described below and include surgical articles configured to cut biological tissue including bone, or surgical articles configured to be implanted within a living subject.

An inventive surgical article is a composition of tungsten carbide, nickel, with a percentage of additional metal carbides present. A typical composition of the present invention in total weight percentages is WC 85 to 95%, $Cr_3C_2$ and $Mo_2C$ each alone or in combination being present from 0 to 2%, and Ni constituting the remainder. The composition is formed to have an mean grain size of between 200 and 1200 nm with a particle dispersion index (PdI) corresponding to (the square of the standard deviation)/(mean grain size) of between 0.02 and 1.2. In some inventive embodiments the PdI is between 0.02 and 0.6, while in other embodiments the PdI is between 0.02 and 0.2. In some embodiments, VC is present in 0% to 1% of the composition. In specific embodiments, the mean grain size is between 600 and 1000 nm.

Figure 1A:
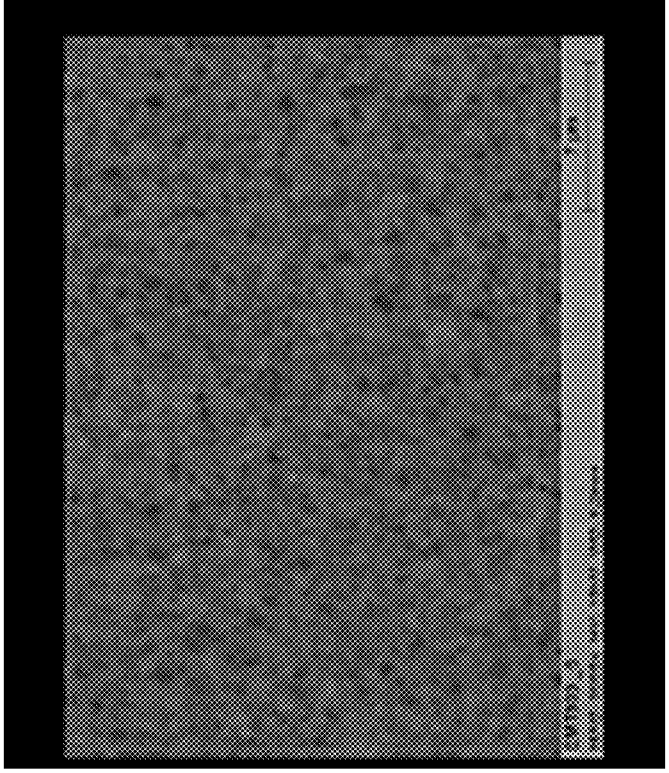
FIG. 1A is a scanning electron micrograph (SEM) of an inventive surgical article in which the scale bar represents 7 microns.
Figure 1C:
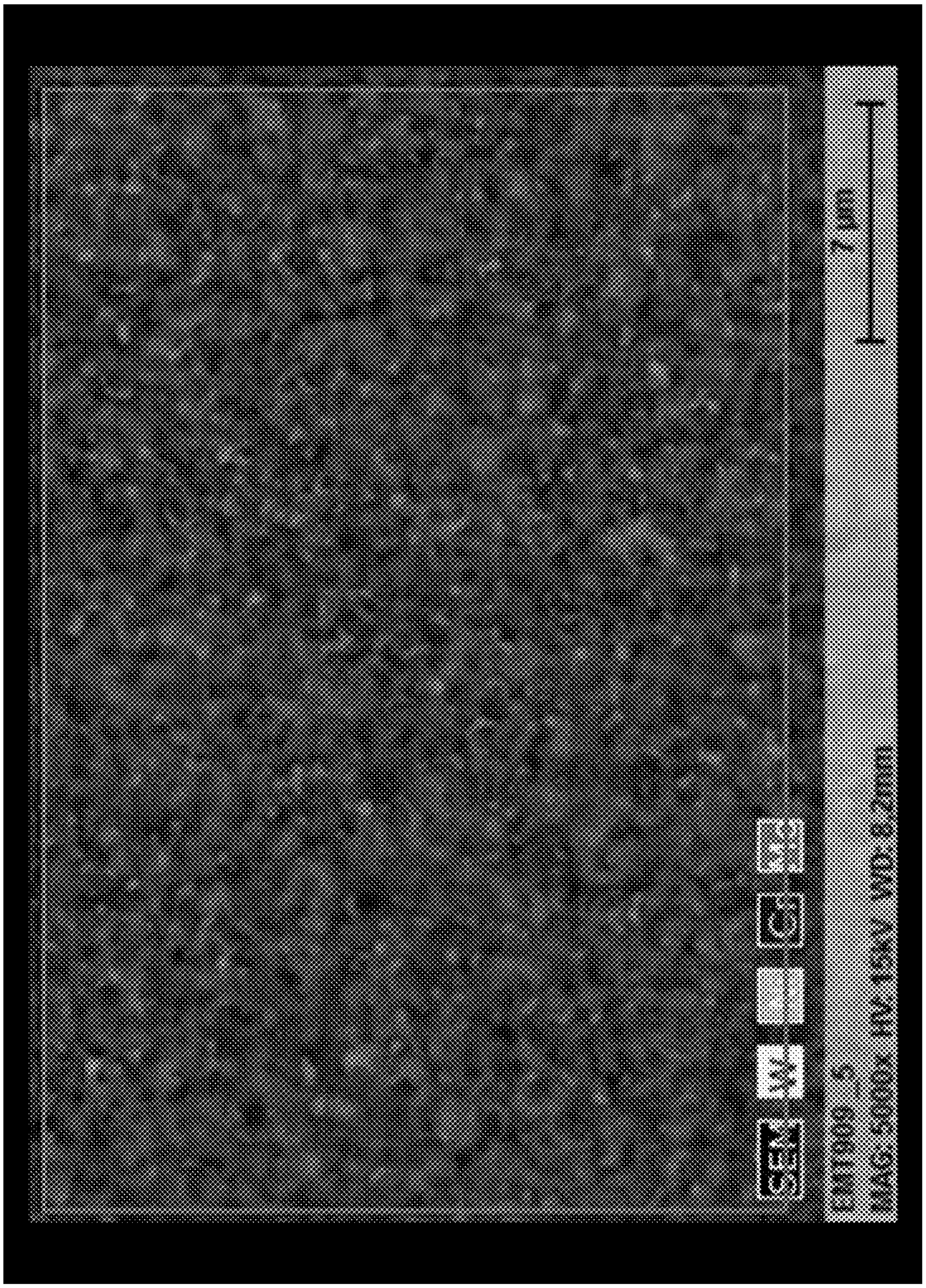
FIG. 1C is an overlay of the false colors of FIG. 1B onto the image of FIG. 1A for tungsten, nickel, chromium, and molybdenum.
Figure 1D:
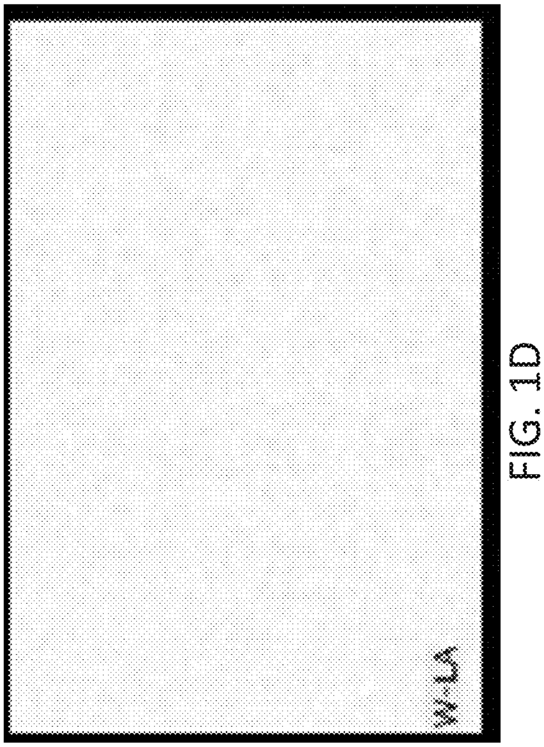
FIGS. 1D-1G are single color overlays of the elemental concentration of tungsten (FIG. 1D), nickel (FIG. 1D), chromium (FIG. 1D), and molybdenum (FIG. 1D) onto the image of FIG. 1A, based on the K-level and L-level emission lines in KeV per FIG. 1B.
Figure 1E:
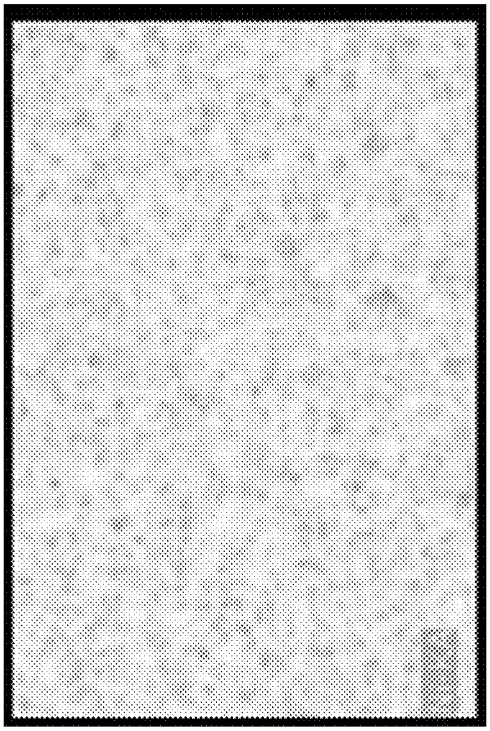
Figure 1F:
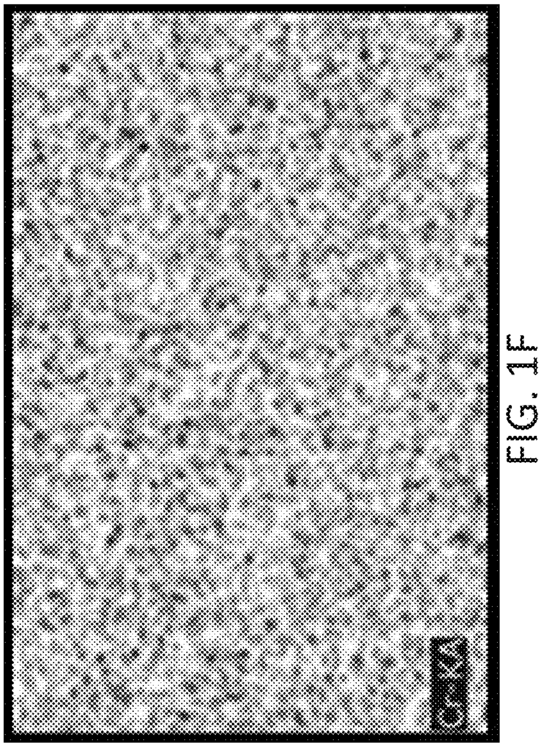
Figure 1G:
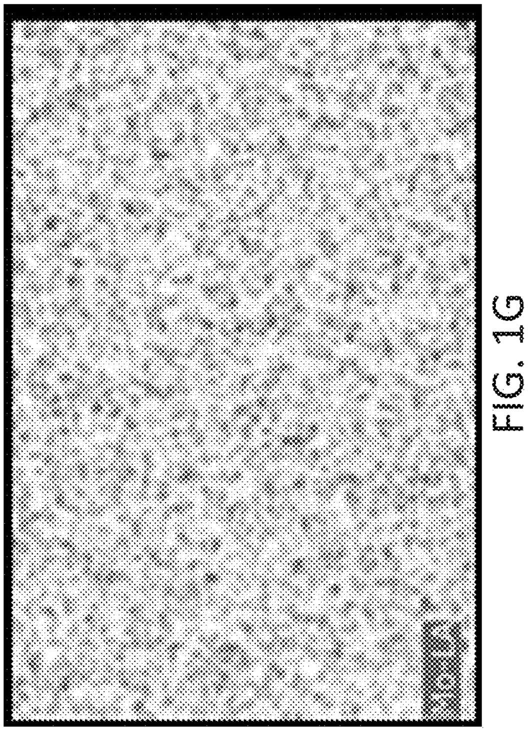

An exemplary composition of an inventive article has the grain structure as shown in the SEM of FIG. 1A where the scale bar denotes 7 microns at a magnification of 5000× and an emission voltage of 15 kV and a working distance (WD) of 8.2 mm. The energy dispersive spectroscopy plot thereof is shown in FIG. 1B and provides the heavy atom (non-carbon) content of the composition. FIGS. 1D-1G are single false color overlays of the elemental concentration of tungsten (FIG. 1D), nickel (FIG. 1D), chromium (FIG. 1D), and molybdenum (FIG. 1D) onto the image of FIG. 1A, based on the K-level and L-level emission lines in KeV per FIG. 1B. The fine grain size, PdI, and homogeneity of the metals in spite of the large differences in relative abundance that characterize an inventive article are noted in FIGS. 1D-1G.

To form a composition for an inventive surgical article, tungsten carbide, nickel and the other metal carbides are combined with elemental carbon and milled and admixed. The resulting mixture is then shaped, debindered at a temperature of between 700° C. and 1100° C., and then exposed to a sintering temperature of the mixture at 1200-1700° C., with a holding time of 10-200 min. In some embodiments the sintering is vacuum sintering under the conditions of 13.3-26.0 Pa. The resulting piece is straightened and exposed to conventional finishing procedures to form an inventive surgical article.

An inventive surgical article has the attributes of high hardness, high impact toughness, wear resistance, and unexpectedly high implantable biocompatibility. The characteristics imparted to the surgical article by this composition are: a density of >14 g/cm$^3$, and a hardness≥1400 HV30 as measured by ISO 3878.

An inventive surgical article operative herein has the shape that illustratively includes an end effector adapted to be coupled to a power tool or a robotic driver; cutter sleeve; a bone clamp; hip implants (total hip and re-surfacing implants); knee implants (total knee and uni-compartmental implants); a shoulder implant; an ankle implant; an elbow implant; a spinal implant; a bone screw; a probe, a pointer, a bone pin; a trauma plate; and a dental drill bit. Other non-orthopedic implants are also contemplated, such as the components for heart implants (e.g., pacemakers). While in some inventive embodiments, a surgical article is formed from a single piece of the composition thereby precluding joints, in other inventive embodiments, a surgical article has a tissue contacting portion formed of the composition and other portions of the surgical article are formed of other materials. By way of example of this latter embodiment, a cutting edge is formed of the composition and the cutting edge or head is joined to a shank formed of conventional materials such as stainless steel or titanium.

FIGS. 2A-2D illustrate an inventive surgical article as a surgical end effector, shown generally at 10. This particular article is a bone drill assembly that is often used to mill bone that is surrounded by soft tissue. It should be understood inventive end effectors are designed to perform various types of surgical procedures, including non-endoscopic, open cut procedures, as well as endoscopic procedures regardless of whether performed manually or under robotic control.

Figure 2A:
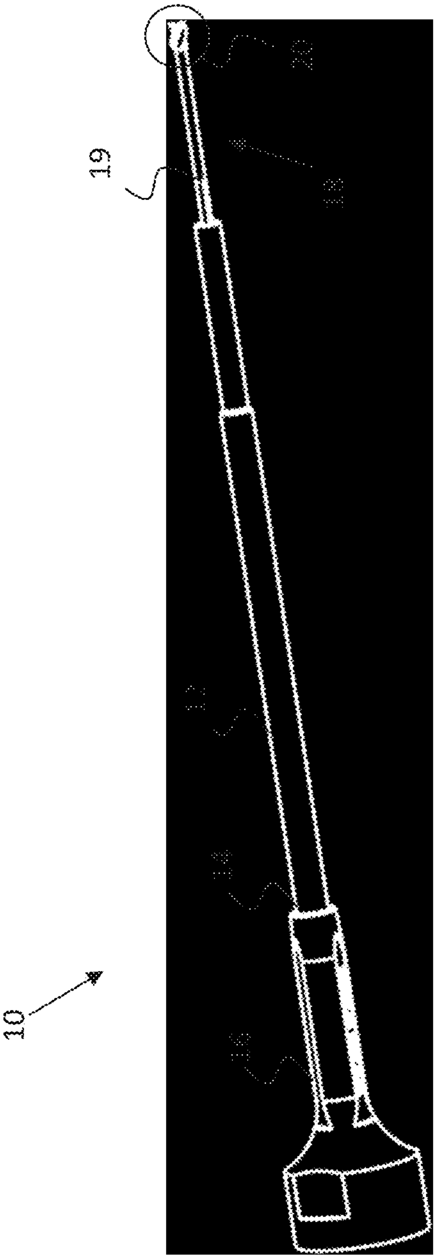
FIG. 2A is a perspective view of an inventive end effector with a circle bounding a region for magnification.
Figures 2B, 2C, 2D:
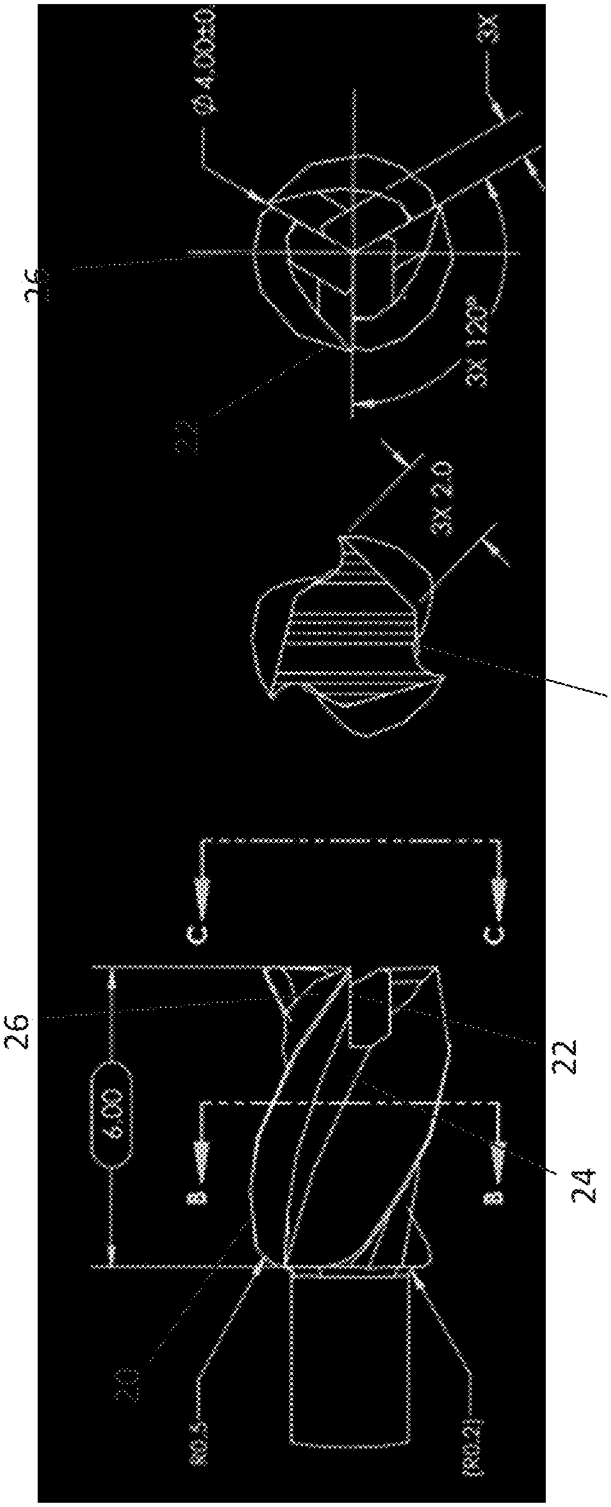
FIG. 2B is the magnified side view of the region of FIG. 2A.
FIG. 2C is a cross sectional view of the FIG. 2B along line B-B.
FIG. 2D is a cross sectional view of the FIG. 2B along line C-C.
Figure 3E:
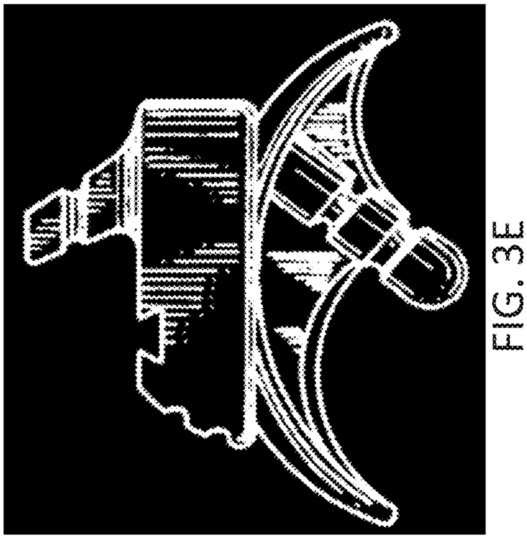
FIG. 3E is a perspective view of an inventive surgical article in the form of ankle implants.
Figure 3G:
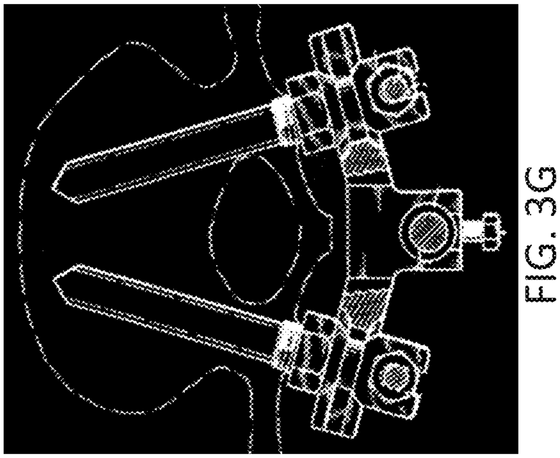
FIG. 3G is a perspective view of an inventive surgical article in the form of spinal implants.
Figure 3D:
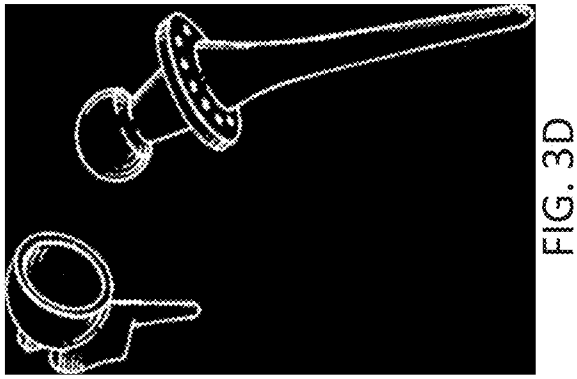
FIG. 3D is a perspective view of an inventive surgical article in the form of shoulder implants.
Figure 3F:
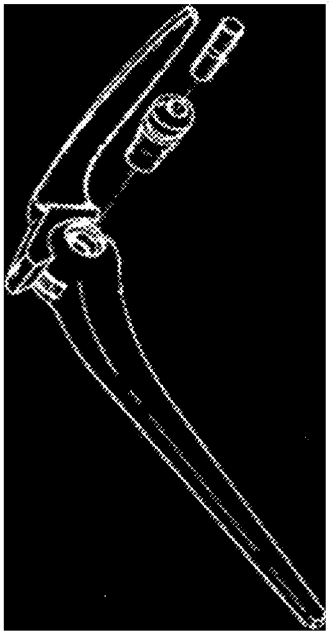
FIG. 3F is a perspective view of an inventive surgical article in the form of elbow implants.
Figure 3I:
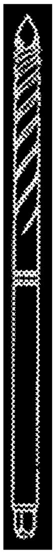
FIG. 3I is a perspective view of an inventive surgical article in the form of a bone pin.
Figure 3K:
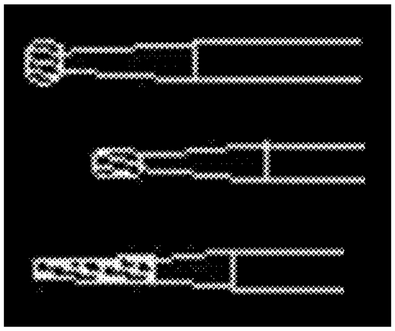
FIG. 3*k* is a perspective view of an inventive surgical article in the form of dental drill bits.
Figure 3H:
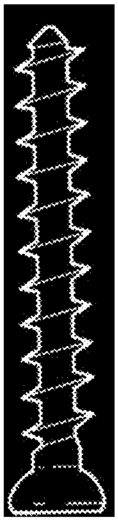
FIG. 3H is a perspective view of an inventive surgical article in the form of a bone screw.
Figure 3J:
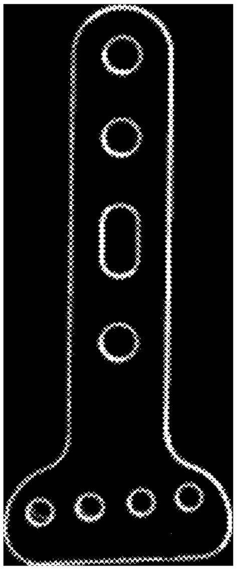
FIG. 3J is a perspective view of an inventive surgical article in the form of a trauma fracture plate.

The depicted end effector 10 has a sleeve 12. The proximal end 14 of the sleeve 12, the end opposite the distal end, is coupled to a hub 16. The hub 16 is adapted to releasably couple the end effector 10 to a powered rotation device (not shown) such as a motor, an orthopedic drill, and/or robotic arm. A surgical cutter 18 having a shaft 19 terminating at a tissue contacting structure 20 is formed of the composition. The shaft 19 of the surgical cutter 18 is housed inside and supported by the sleeve 12 and directly couples to the powered rotation device to rotate the surgical cutter 18. The tissue contact structure 20 as depicted has a cutting edge 22 with an adjacent flute 24 and a flank 26. The tissue contacting structure 20 shown in FIG. 2A is shown in magnified side, cross sectional, and front views in FIGS. 2B, 2C, and 2D; respectively. It is appreciated that other surgical articles with conventional tissue contacting structures also benefit from the properties of the tungsten carbide in nickel-based composition of the present invention. These illustratively include smooth trocars, threaded trocars, Kirschner pins. It is appreciated that such surgical articles are operated in both unidirectional rotation, bidirectional rotation, and oscillatory movement pattern to perform a desired surgical procedure and as all generate frictional heating of tissue, benefit from the use of surgical articles formed according to the present invention.

An inventive surgical article has been found to have levels of biocompatibility that render the composition suitable to be formed into implants; this in spite of the conventional concerns that nickel is considered a heavy metal disfavored as an implant substance. Additionally, the hardness of a surgical article and wear properties afford an attractive implant with an extended operational life relative to the same shaped implant formed of conventional materials such as stainless steel or titanium alloys. Surgical articles operative as tools and implants as shown in FIGS. 3A-3K illustratively include; a bone clamp; hip implants (total hip and re-surfacing implants); knee implants (total knee and uni-compartmental implants); a shoulder implant; an ankle implant; an elbow implant; a spinal implant; a bone screw; a bone pin; a trauma plate; and a dental drill bit, respectively.

An inventive surgical article shaped to form an implant is coated in some inventive embodiments with a surface coating. Surface coatings operative herein include, antimicrobials, cellular adhesion promoters, osteocyte stimulation promoters, vascular growth factors, bioactive growth factors, or a combination thereof.

With respect to inventive surgical articles shaped to form implants that contact intact bone or a complementary to excised bone tissues to expose a bone tissue surface, an implant is in some embodiments modified to promote conduction. Bone conduction, the growth of bone on an implant surface (synonymously referred to in the literature as osseoconduction) depends on the action of differentiated bone cells. These cells may originate either in pre-existing preosteoblasts/osteoblasts that are activated by surgical trauma or in cells recruited from primitive mesenchymal cells by osteoinduction. Various types of bone growth factors are necessary for bone formation. Furthermore, bone growth, including bone conduction, does not occur without a proper blood supply and therefore growth factors that are both angiogenic and mitogenic that can be added to the implant or stimulations at the implant-body interface appear to promote osseointegration in the present invention. Growth factors that regulate bone tissue in one way or another include insulin-like growth factor (IGF I, II), vascular endothelial growth factor (VEGF), fibroblast growth factor (FGF), TGF-β, platelet-derived growth factor (PDGF) and combinations thereof are illustrative of growth factors that physically coat or are covalently bonded to the surfaces of the implant to which osseointegration is desired. It is appreciated that a slow release matrix contains a growth factor is operative herein; such matrices include Choukroun's platelet-rich fibrin (PRF).

An inventive implant can be stabilized by coating portions of the implant with any of the aforementioned. It is appreciated that even in instances when osseointegration does not occur to any appreciable degree, bone conduction by forming a new layer bone at the interface with an implant surface imparts a desired implant stabilization according to the present invention. The bone-implant interface in osseointegration according to the present invention typically has an amorphous layer from 20 to 500 nm thick. Collagen and calcified tissue are typically found in this interface.

EXAMPLES

The present invention is further detailed with respect to the following nonlimiting example that is provided to further illustrate the preparation of inventive articles and certain attributes associated therewith.

Example—Assessment of Biocompatibility

The albino guinea pig has historically been used in skin sensitization tests and is generally accepted as the most appropriate animal model for human allergic contact dermatitis. Eleven test male guinea pigs, (*Cavia porcellus*), Hartley strain (specific pathogen free) of common weight and age (per extract) are injected with the test article extract and Freund's complete adjuvant (FCA), and six guinea pigs (per extract) are injected with the corresponding control blank and FCA. The animals are maintained under conventional test animal conditions. On Day 6, the dorsal site is re-shaved and sodium lauryl sulfate (SLS) in mineral oil is applied. The day after the SLS application, the test animals are topically patched with the appropriate test extract and the control animals are patched with the corresponding control blank. The patches are removed after 48±2 hours of exposure. Following an approximate two-week rest period, the animals are topically patched with the appropriate test extract and corresponding control blank. The patches are removed after 24±2 hours of exposure. The dermal patch sites are observed for erythema and edema 24 2 and 48±2 hours after patch removal. Each animal is assessed for a sensitization response based upon the dermal scores. The test results are based upon the percentage of animals exhibiting a sensitization response.

The test article per FIGS. 2A-2D has an inventive composition of 90.5 wt. % WC, 8.5 wt. % Ni, and 1% total of the other carbides. The test article remained intact, is placed into extraction vessels, and prepared at a ratio of 3 $cm^2$/1 mL of extraction vehicle.

The extraction mixtures and corresponding control blanks are incubated for 72±2 hours at 50±2'C. At the start of the extraction, the solutions appeared clear and free of particulates. The extracts are agitated during the course of the extraction period. At the end of the extraction period, the vessels are shaken well and the liquid aseptically decanted into a sterile vessel. See Table 2 for extract observations. The particulates are allowed to settle prior to dosing. After decanting, the extracts are not filtered prior to use. The extracts are maintained at room Second Induction/Topical Application: On Day 6, the injection site area is clipped free of fur and treated with 0.5 mL of 10% (w/w) SLS prepared by mixing solid SLS with mineral oil. The day following the SLS treatment, the remaining SLS residue is gently wiped from the area with gauze.

On Day 7, the test article extracts (0.3 mL) are applied to a 2 cm×4 cm piece of filter paper to saturation and applied after SLS removal. The patch is secured to the site with non-permeable tape on the test animals and the trunk wrapped with elastic bandage and hypoallergenic tape. The control animals received a similar patch with the control vehicles. Freshly prepared extracts are used for this administration. This preparation is removed after 48±2 hours of application.

Challenge Patch/Topical Application: Fourteen days after completion of the topical induction phase, the challenge procedure is initiated. A 2 cm×2 cm filter paper patch is saturated with 0.3 mL of freshly prepared test article extract and applied to the fur clipped right flank of each test animal. A 2 cm×2 cm filter paper patch is saturated with 0.3 mL of freshly prepared control vehicle and applied to the fur clipped left flank of each test animal.

The negative control animals are challenged in an identical fashion with similarly prepared patches. The left side of each animal is patched with a filter paper patch saturated with 0.3 mL of control vehicle. The right side is patched with a filter paper patch saturated with 0.3 mL of the prepared test article extract applied to the fur clipped flank. The trunk of each animal is wrapped for 24±2 hours with elastic bandage and hypoallergenic tape.

The following day (24±2 hours) after challenge exposure, the patches are removed and the site is wiped gently with a 70% isopropyl alcohol soaked gauze sponge prior to each scoring period. The challenge sites are observed for irritation and sensitization reaction, as indicated by erythema and edema. Daily challenge observation scores are recorded 24±2 and 48±2 hours after patch removal in accordance with the classification system for skin reactions in Table 5. Daily animal health observations are recorded throughout the study period.

No erythema or edema ("0" on Magnusson and Kligman scale) is observed in any animals exposed to the test article in any form of exposure, where erythema is defined as redness and edema is defined as a swelling at the challenge site. Any other adverse changes at the skin sites are recorded and reported. None of the negative control animals challenged with the control vehicles are observed with a sensitization response greater than '0'

Example—Assessment of Material and Cutting Properties

The cutting performance between a stainless steel cutter and a WC cutter made of the composition described herein was studied. The WC cutter and stainless steel cutter were of the same design as showed in FIG. 2A having a shaft and a burr head (tissue contacting structure). In one experiment, the volumetric removal rate was examined. Cutting performance can be characterized by the efficiency of the material removal rate. Both cutters were subjected to cut different density foam blocks under the same operating conditions (spindle speed and feed rate). The different foam block had densities of 15 pounds per cubic feet (pcf), 30 pcf, 50 pcf, and 70 pcf. The WC cutter's performance for a 5 millimeter (mm) burr head matched that of the stainless steel cutter. In some cases, the removal rate was 3% to 5% greater for the WC cutter. No damage to the cutter heads was visualized.

Static testing of the stainless steel cutter and the WC cutter was also compared. Deflection (mm), torsion strength (N/m), tensile strength (N) were examined. For deflection, each cutter was subjected to a 207.4 N load. The WC cutter had a 3 point bend deflection of approximately (~)0.6 mm, while the stainless steel cutter had a deflection of ~2.75 mm. For torsion strength, the WC cutter exhibited a strength of ~5.2 N/m, while the stainless steel cutter exhibited a strength of ~2.7 N/m. For tensile strength, the WC cutter exhibited a strength of ~5600 N, while the stainless steel cutter exhibited a strength of ~2400 N.

Overall, in the tests performed, the WC cutter has shown to be more durable due to the composition of the cutter. The WC cutter showed improved toughness when cutting the foam blocks and showed less damage than the stainless steel cutter during destructive testing. In addition, due to the superior properties of the WC cutter, the need for a sleeve to hold and support the cutter may no longer be needed.

Other Embodiments

While at least one exemplary inventive embodiment has been presented in the foregoing detailed description, it should be appreciated that a vast number of variations exist. It should also be appreciated that the exemplary inventive embodiment or exemplary inventive embodiments are only examples, and are not intended to limit the scope, applicability, or configuration of the described inventive embodiments in any way. Rather, the foregoing detailed description will provide those skilled in the art with a convenient roadmap for implementing the exemplary inventive embodiment or exemplary inventive embodiments. It should be understood that various changes may be made in the function and arrangement of elements without departing from the scope as set forth in the appended claims and the legal equivalents thereof.

The invention claimed is:

1. A surgical article comprising:

a composition having a desired shape and a mean grain size, said composition consisting essentially of by weight: WC present from 85 to 95 total weight percent; $Cr_3C_2$ and $Mo_2C$ each alone, or in combination being present from 0 to 2 total weight percent, and Ni constituting the remainder; the average grain size being between 200 and 1200 nm with a particle dispersion index of between 0.02 and 1.2 and a density of >14 g/$cm^3$, and a hardness ≥1400 HV30.

2. The surgical article of claim 1 wherein the particle dispersion index is between 0.02 and 0.6.

3. The surgical article of claim 1 wherein $Cr_3C_2$ and $Mo_2C$ are all present and constitute in total more than 0 and less than 1 total weight percent.

4. The surgical article of claim 1 wherein the desired shape is configured to cut, mill, burr, or otherwise remove or cut tissue from a subject.

5. The surgical article of claim 1 wherein the desired shape is a smooth trocar, a threaded trocar, a Kirschner pin, a drill bit, a rongeur, an end-effector, a burr, a cutter, or a surgical saw blade.

6. The surgical article of claim 1 wherein the desired shape is a cutter sleeve, a bone clamp, a hip implant, a knee implant, a shoulder implant, an ankle implant, an elbow implant, a spinal implant, a screw, a pin, an intramedullary nail, a probe, a pointer, or a trauma plate.

7. The surgical article of claim 1 further comprising a surface coating wherein the desired shape is a surgical drill bit, an orthopedic implant, a dental drill bit, a drill guide, a saw guide, a screw, or a pin.

8. The surgical article of claim 1 wherein the composition further comprises VC present from 0 to 1 percent by total weight.

9. A method of cutting tissue of a subject in the course of a surgical procedure comprising:

providing a surgical article according to claim 1, wherein the surgical article comprises a tissue contacting portion for engaging the tissue of the subject.

10. The method of claim 9 wherein said surgical article is rotated or oscillated.

11. The method of claim 9 further comprising selectively coupling said surgical article to a robotic arm prior to engaging the tissue.

12. A method of modifying tissue of a subject in the course of a surgical procedure comprising:

providing a surgical article according to claim 1 for placement in contact with the tissue of the subject, wherein said surgical article is configured to be retained in vivo and in contact with the tissue of the subject.

13. The method of claim 12 further comprising removing a portion of the tissue from the subject to expose a tissue surface and said surgical article is complementary to the tissue surface.

14. The method of claim 13 wherein said removing step is performed robotically.

* * * * *